United States Patent [19]

Kawahara et al.

[11] Patent Number: 5,389,071
[45] Date of Patent: Feb. 14, 1995

[54] INFUSION METHOD HAVING A PLURALITY OF DELIVERY PATTERNS

[75] Inventors: Masafumi Kawahara, Nara, Japan; Donald J. Classey, Waukegan, Ill.; Kenneth M. Lynn, McHenry, Ill.; Michael Gluth, Arlington Heights, Ill.; Grace M. Esche, Algonquin, Ill.; Joseph B. Matthews, Grayslake, Ill.

[73] Assignee: Sharp Kabushiki Kaisha, Osaka, Japan

[21] Appl. No.: 42,015

[22] Filed: Apr. 2, 1993

[30] Foreign Application Priority Data

Apr. 3, 1992 [JP] Japan .................. 4-081959

[51] Int. Cl.[6] .............. A61M 31/00; A61M 5/30
[52] U.S. Cl. ............................ 604/51; 604/53; 604/67; 128/DIG. 12
[58] Field of Search ............... 604/48, 49, 51-53, 604/65-67, 131, 151-155, 246; 128/DIG. 12, DIG. 13

[56] References Cited

U.S. PATENT DOCUMENTS

| 4,464,172 | 8/1984 | Lichtenstein | 604/65 |
| 4,776,842 | 10/1988 | Franetzki et al. | 604/67 |
| 4,810,243 | 3/1989 | Howson | 604/31 |
| 4,846,792 | 7/1989 | Bobo, Jr. et al. | 604/50 |
| 5,041,086 | 8/1991 | Koenig et al. | 604/65 |
| 5,100,380 | 3/1992 | Epstein et al. | 604/67 |
| 5,104,374 | 4/1992 | Bishko et al. | 604/31 |

FOREIGN PATENT DOCUMENTS

6363 1/1988 Japan .

Primary Examiner—C. Fred Rosenbaum
Assistant Examiner—Adam J. Cermak

[57] ABSTRACT

An infusion apparatus incorporates a RAM which has a first storage section for storing only one delivery pattern defining an infusion rate and a volume to be infused at the infusion rate, and a PDP storage section for storing a plurality of delivery patterns. In a one-pattern delivery mode, an infusion fluid is delivered according to the only one delivery pattern read out from the first storage section by a CPU. Therefore, infusion is performed at the same rate from the beginning to the end. In a PDP (Program Delivery Profile) mode, an infusion fluid is delivered according to the plurality of delivery patterns read out in sequence from the PDP storage section. Therefore, infusion is performed at various rates. One of the one-pattern delivery mode and the PDP mode is selected by an operator through operation of a mode selector in consideration of factors such as the kind of medication and the condition of the patient.

4 Claims, 9 Drawing Sheets

INFUSION METHOD HAVING A PLURALITY OF DELIVERY PATTERNS

BACKGROUND OF THE INVENTION

1. Field of the Invention

The present invention relates to an infusion apparatus capable of infusing medication into a patient in a pattern appropriate for the kind of medication and the condition of the patient.

2. Description of the Prior Art

Figure 6:
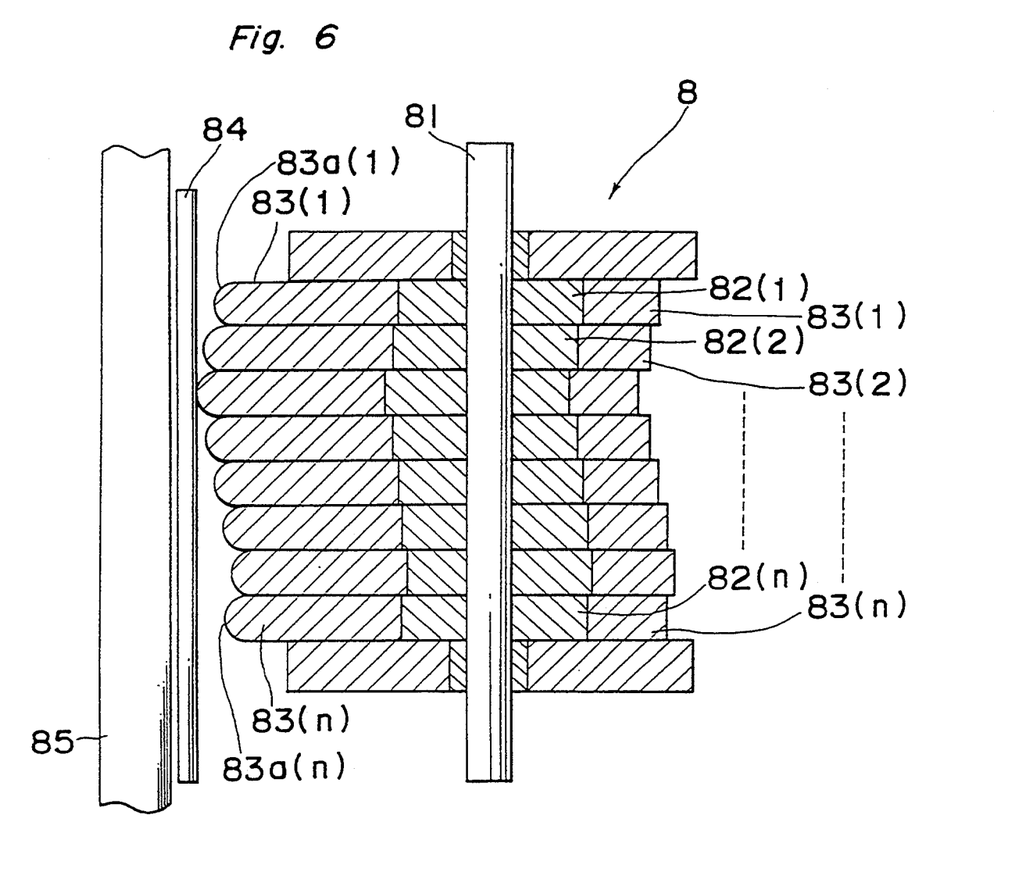
FIG. 6 is a cross-sectional view of a pump mechanism commonly used in infusion apparatuses and also used in the embodiment of FIG. 1.

Infusion apparatuses are used for administering medication such as a saline solution into a vein of a patient. A generally known infusion apparatus is of an electromechanical positive pressure peristaltic type provided with a pump mechanism for peristaltically delivering medication. FIG. 6 shows an example of such a pump mechanism. The pump mechanism, generally indicated by numeral 8 in FIG. 6, has n pressure fingers 83(1), 83(2), . . . , 83(n) with their ends 83a(1), . . . , 83a(n) confronting a door 85 of a housing of the infusion apparatus, and n cams 82(1), 82(2), . . . , 82(n) associated with the n pressure fingers 83(1), 83(2), . . . , 83(n). The cams 82(1), 82(2), . . . , 82(n) are engaged with a shaft driven by a not-shown stepping motor, with their phases shifted from one another. The pressure fingers 83(1), 83(2), . . . , 83(n) are individually moved in sequence toward the door 85 by the associated cams 82(1), 82(2), . . . , 82(n) with rotation of the shaft 81 so as to push an administration tube 84 set in the pump mechanism against the door 85. By so pressing the administration tube 84 against the door 85 from above downward with the fingers 83(1), 83(2), . . . , 83(n), medication supplied from an administration set into the administration tube 84 is peristaltically delivered to a patient.

Figure 7:
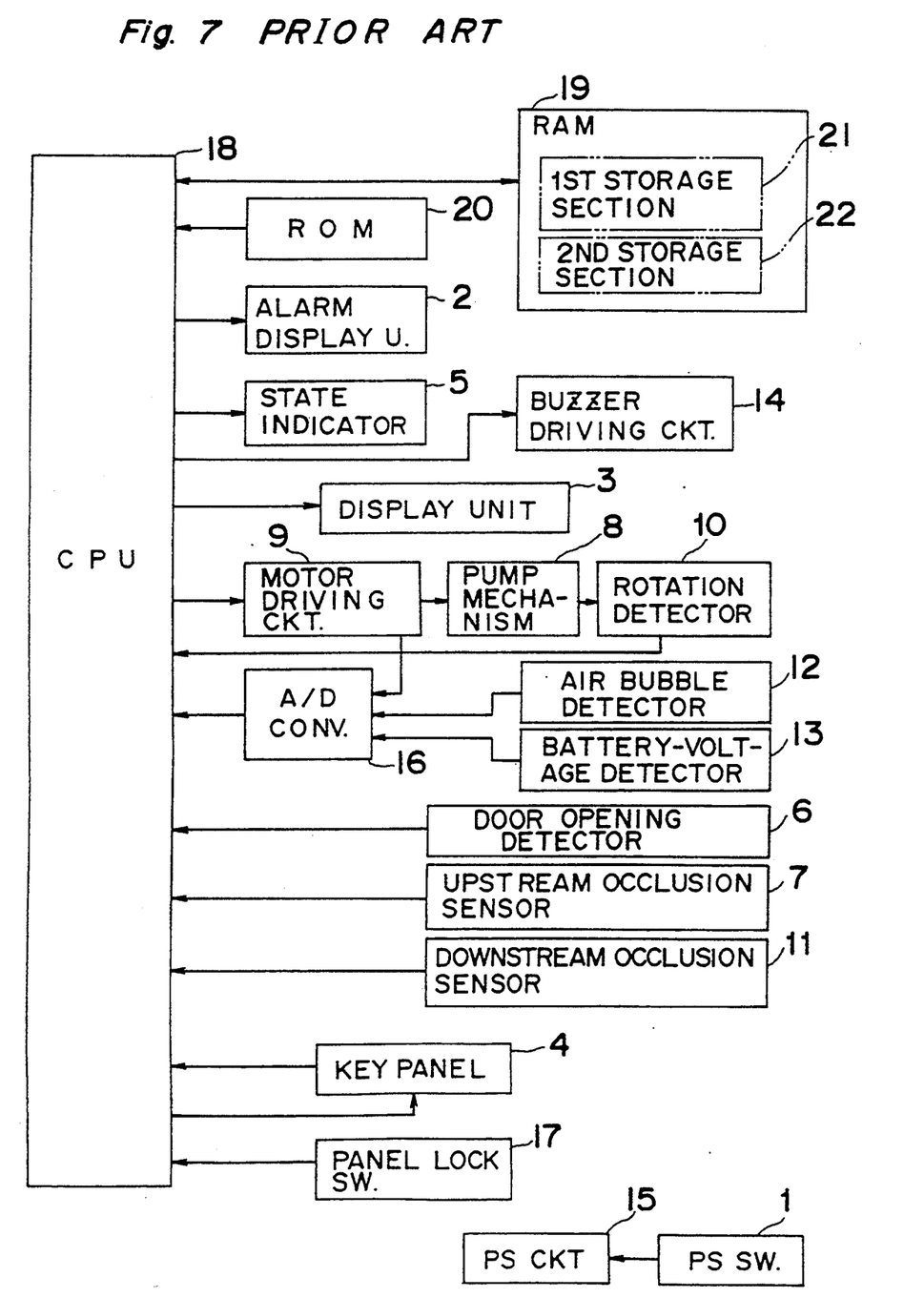
FIG. 7 is a block diagram of a conventional infusion apparatus.
Figure 9:
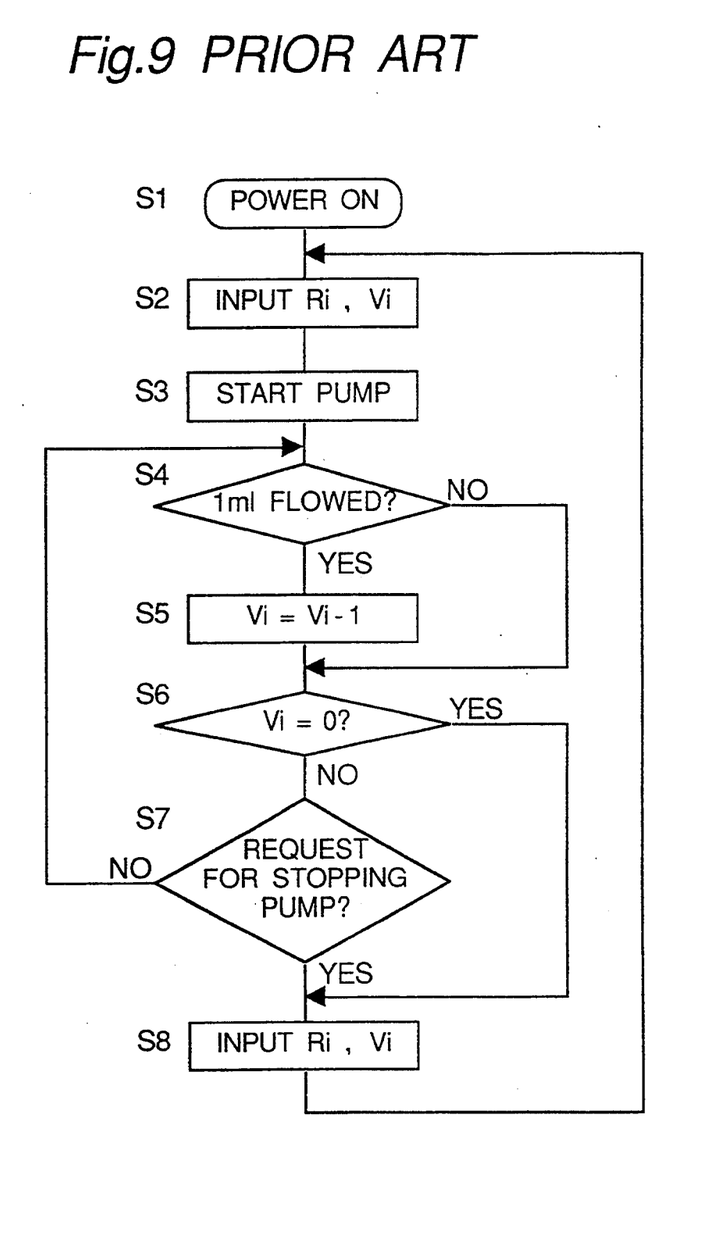
FIG. 9 is a flowchart of the operation of the conventional infusion apparatus of FIG. 7.
Figure 10:
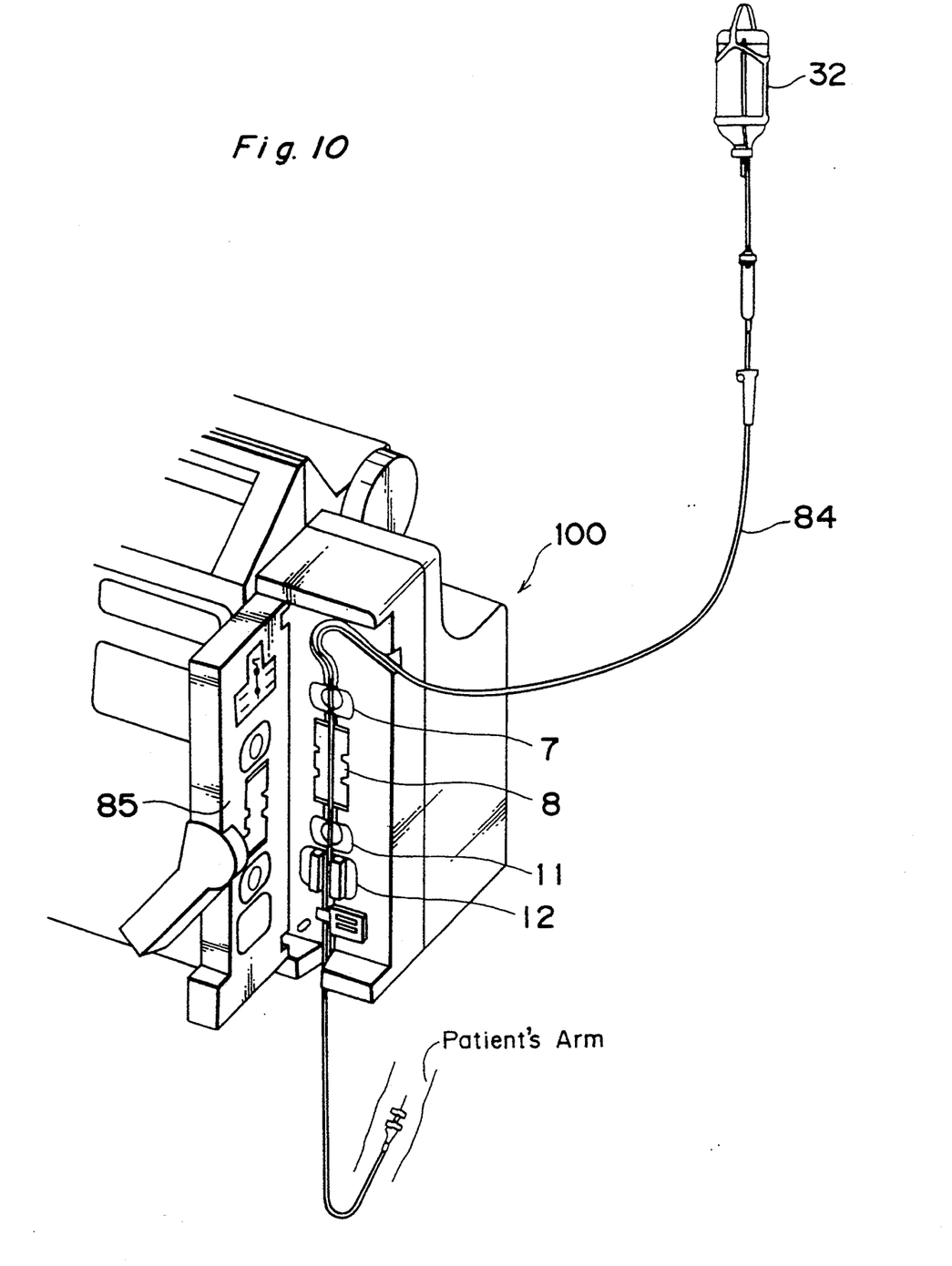
FIG. 10 is a perspective view of a common infusion apparatus.

FIG. 7 shows a block diagram of a conventional infusion apparatus of the above-mentioned type, FIG. 9 is a flowchart showing the operation of the infusion apparatus of FIG. 7, and FIG. 10 is a perspective view Showing a part of the infusion apparatus. It is to be noted that because an infusion apparatus of the present invention described later has a similar appearance, FIG. 10 is also used to illustrate the infusion apparatus of the present invention.

Referring to FIG. 7 and FIG. 10, a power switch 1 turns on the infusion apparatus, generally indicated by numeral 100, when pressed. An alarm display unit, designated by numeral 2, displays all alarm messages for errors detected in the infusion apparatus. A display unit, designated by numeral 3, displays infusion-related parameters such as a volume of infusion fluid delivered per unit time (simply referred to as "infusion rate" or "delivery rate" below), a total volume of infusion fluid to be delivered at the infusion rate (simply referred to as "volume to be delivered" or "volume to be infused" hereinafter), as well as an accumulated volume of the infusion fluid already delivered (referred to simply as "accumulated infusion fluid volume" hereinafter). A key panel, designated by numeral 4, has thereon numeral keys for inputting settings such as the infusion rate and volume to be infused or delivered in order to set values of an operation speed and operation time for the pump mechanism 8, control keys for input assistance, a start key for starting the operation of the pump mechanism 8, a stop key for stopping the operation of the pump mechanism 8, and a call key for requesting various values such as the accumulated infusion fluid volume to be displayed. A state indicator, designated by numeral 5, is a lamp that indicates which state the apparatus is currently in among the states of "alarming", "in operation", and "out-of-operation". A door opening detector, designated by numeral 6, detects whether or not the door 85 has come into an open position in which the administration tube 84 is set in place in the pump mechanism 8. The door opening detector 6 also detects that the door 85 is inadvertently opened while the pump mechanism 8 is in operation. When this error is detected, the operation of the pump mechanism 8 is stopped and an alarm is raised. An upstream occlusion sensor, designated by numeral 7, detects a pressure-reduction state caused by occurrence of any abnormality (e.g., clogged filter) in the administration set disposed between a medical fluid container 32 and the apparatus. A motor driving circuit, designated by numeral 9, drives the stepping motor of the pump mechanism 8 in response to a pulse outputted from a CPU 18. A rotation detector, 10 designated by numeral 10, through detection of the amount of rotation of the stepping motor of the pump mechanism 8 detects that an incremental unit (e.g., 1 ml) of fluid has taken place, and then informs the CPU 18 of it. A downstream occlusion sensor, designated by numeral 11, detects a pressure-rise state within the administration tube 84 located between the apparatus and the patient to detect occurrence of any abnormality such as occlusion occurring within the administration tube 84. When the pressure-rise state is detected, the pump mechanism 8 is stopped and an alarm is raised. An air bubble detector, designated by numeral 12, detects that air bubbles of more than a prescribed amount have entered the administration tube 84. When this is detected, an alarm is raised while the pump mechanism 8 is stopped so that the bubbles are prevented from entering into the patient's body. A battery-voltage detector, designated by numeral 13, detects any battery-voltage drop of a lead battery (not shown) used as a backup of an AC power supply. When this battery-voltage drop is detected, operation of the pump mechanism 8 is stopped while an alarm is raised. The lead battery is charged by a power supply circuit 15 when the apparatus is fed power from the AC power supply. A buzzer driving circuit, designated by numeral 14, generates a buzzer sound for informing doctors and nurses of the fact that the infusion apparatus has entered into the alarming state. The power supply circuit 15 supplies power to all the circuits of the infusion apparatus. An analog-to-digital converter, designated by 16, converts analog data such as the voltage resulting from voltage conversion of a current supplied to the motor of the pump mechanism 8, the air bubble detector output level, and the battery voltage level into digital values, and inputs them into the CPU 18. A panel lock switch, designated by numeral 17, serves to render the panel keys and the power key input-inhibited so that the infusion apparatus will not be operated by unauthorized personnel. The CPU 18 controls the operation of the overall infusion apparatus. A RAM (memory section), designated by numeral 19, includes a first storage section 21 for storing an infusion rate and volume to be infused, those parameters having been key-inputted, a second storage section 22 for storing various types of data used for arithmetic operations by the CPU 18. A ROM (program section), designated by numeral 20, contains a program for operating the CPU 18.

Figure 8:
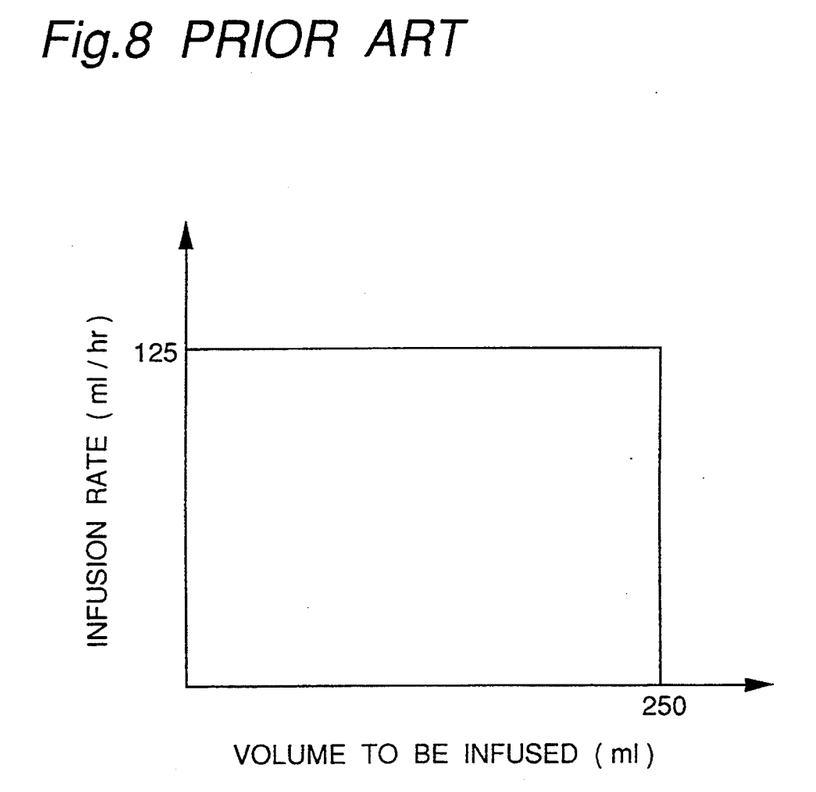
FIG. 8 is a graph showing a delivery pattern used in the conventional infusion apparatus of FIG. 7.

FIG. 8 shows an example of a pattern of combination of the infusion or delivery rate and the volume to be infused or delivered (this pattern will be referred to as "delivery pattern" below), which is stored in the first storage section 21 of the RAM 19. In FIG. 8, the infusion rate is plotted on the axis of ordinates and the volume to be infused is plotted on the axis of abscissas. In this case, the infusion rate is 125 ml/hr, and the volume to be infused is 250 ml.

The following describes the operation of the above conventional infusion apparatus with reference to a flowchart shown in FIG. 9.

When the infusion apparatus 100 is turned on at step S1, the apparatus 100 requests an operator, more specifically a doctor or nurse, to input parameter values of the infusion rate and volume to be infused. Therefore, in response to this request, the operator inputs values of the infusion rate Ri and volume to be infused Vi, at step S2, according to the kind of medication to be administered and the therapeutic procedures selected. The pump is started at step S3 when a command to start the pumping operation is key-inputted, the pump mechanism 8 starts to feed an infusion fluid at the inputted infusion rate. Then, at step S4, it is determined whether or not there was an incremental unit of fluid (1 ml in this case), which is detected by the rotation detector 10. If yes, the program proceeds to step S5 at which 1 is subtracted from the initially inputted value of the volume to be infused Vi, and a new value obtained through this subtraction is set as a renewed volume (Vi=Vi−1). Next, at step S6, it is determined whether or not the volume to be infused Vi has reduced to zero. Vi=0 signifies that all the infusion fluid to be infused in this infusion operation has been delivered. Therefore, when it is determined that Vi=0 at step S6, the operation of the pump mechanism 8 is stopped at next step S8. However, even when the remaining volume to be infused Vi is not zero, the pump mechanism 8 is stopped if, at step S7, a corresponding key operation by the operator or an occurrence of some alarm requires stoppage. Then the program returns to step S2 to wait for an input of the next values Ri, Vi of the infusion rate and volume to be infused for the next infusion operation.

The above-mentioned conventional infusion apparatus cannot store more than one delivery pattern as shown in FIG. 8 in the first storage section 21. Some infusion fluids can adversely affect the patient if infused at only a single infusion rate. For example, in some cases, with potent medications, it is desirable to start infusing the medication into the patient little by little at the beginning, then gradually increase the initial infusion rate to a target infusion rate as the patient grows accustomed to the medication, and finally infuse the remaining major part of the medication at the target infusion rate. Also, in some cases, the patient can be adversely affected if infusion is suddenly stopped. This is because the patient's body, into which medication has been infused, cannot quickly adapt itself to the sudden change of condition from the infused state to the non-infused state. In such a case, it is recommendable to gradually reduce the infusion rate to zero in the final stage of the infusion.

However, when such a flexible infusion operation is desired, a single delivery pattern is insufficient. Accordingly, the conventional infusion apparatus having only a single delivery pattern cannot be used to infuse some kinds of medication in some cases, unless the operator, i.e., a doctor or nurse, stays by the apparatus and changes the infusion rate and the volume to be infused.

SUMMARY OF THE INVENTION

The object of the present invention is therefore to provide an improved infusion apparatus capable of storing a plurality of fluid delivery patterns and infusing medication in an infusion fluid into a patient in a pattern appropriate for the medication and the condition of the patient.

In order to achieve the aforementioned object an embodiment of the present invention provides an infusion 10 apparatus for infusing an infusion fluid into a patient through an administration tube, comprising a) a pump mechanism for peristaltically pumping the infusion fluid in the administration tube to deliver the infusion fluid toward the patient, b) inputting means for inputting a value of an infusion rate and a value of a volume to be infused at the infusion rate, both values being used in combination, c) storage means having a storage section for storing a plurality of combinations of values of the infusion rate and values of the volume to be infused, which values being inputted by the inputting means, d) accessing means for reading the plurality of combinations of the values of the infusion rate and volume to be infused in sequence from the storage section, e) controlling means for controlling the pump mechanism to deliver the infusion fluid in accordance with the plurality of combinations of the values read by the accessing means.

In the infusion apparatus having the construction as described above, an operator, more specifically a doctor or nurse, can input in advance a plurality of combinations of values of the infusion rate and the volume to be infused (referred to as "delivery pattern") by the inputting means, in accordance with the kind of medication to be infused and the condition of the patient. And the infusion fluid is delivered at different infusion rates according to the plurality of delivery patterns automatically read out in sequence from the storage means. Therefore, the infusion apparatus of the present invention can infuse even potent medications which could not be infused by the conventional infusion apparatus without manually changing the settings of the single delivery pattern by the operator who was required to be beside the apparatus. Therefore, the infusion apparatus of the present invention is applicable to more types of medication and is adaptable to different patients' conditions. As a result, an enhanced therapeutic effect can be achieved.

The storage means or RAM (random access memory) may further include another storage section for storing only a single delivery pattern. In this case, the apparatus further includes selecting means for selecting one of the following two modes:

1) a one-pattern delivery mode wherein the pump mechanism delivers the infusion fluid in accordance with the single delivery pattern, and
2) a program delivery profile (PDP) mode wherein the pump mechanism delivers the infusion fluid in accordance with the plurality of delivery patterns in the storage section.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

The following describes the present invention with reference to an embodiment shown in the attached drawings.

Figure 1:
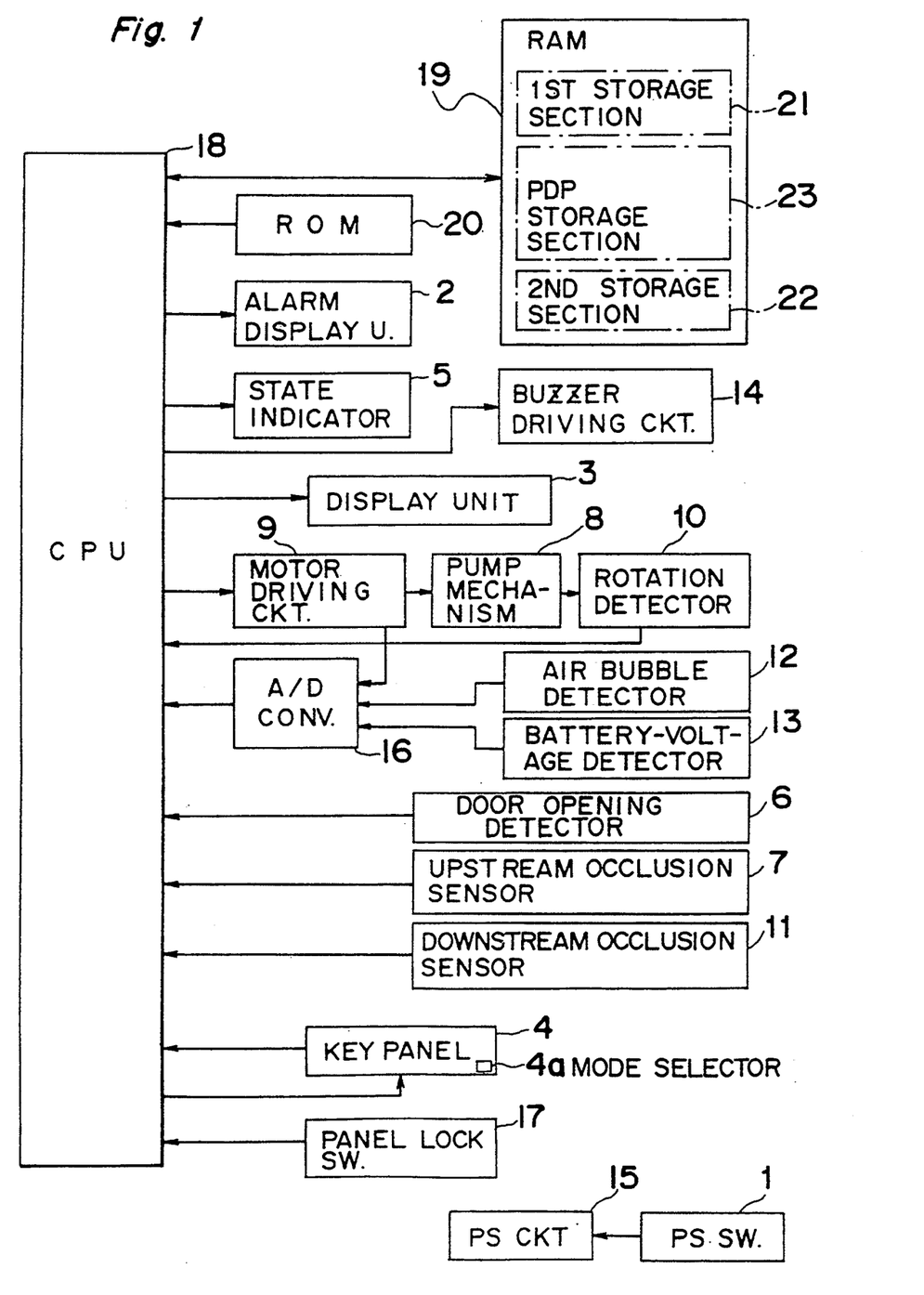
FIG. 1 is a block diagram of an infusion apparatus according to an embodiment of the present invention.

FIG. 1 is a block diagram of an infusion apparatus according to an embodiment of the present invention. In FIG. 1, parts similar to the parts of the conventional infusion apparatus of FIG. 7 are indicated by the same reference numeral used in FIG. 7 and a detailed description on those parts is omitted here.

The infusion apparatus of the present embodiment differs from the conventional apparatus of FIG. 7 in that a RAM 19 incorporated in the infusion apparatus of the present invention further has a PDP (Program Delivery Profile) storage section 23 capable of storing a plurality of delivery patterns, that the delivery patterns can be inputted from the key panel 4, and that the CPU 18 controls the infusion operation using the plural delivery patterns in response to a command inputted from the key panel 4. In addition, the key panel 4 of the infusion apparatus of the present embodiment further include a mode selector 4a for selecting an operation mode as described later.

Figure 2:
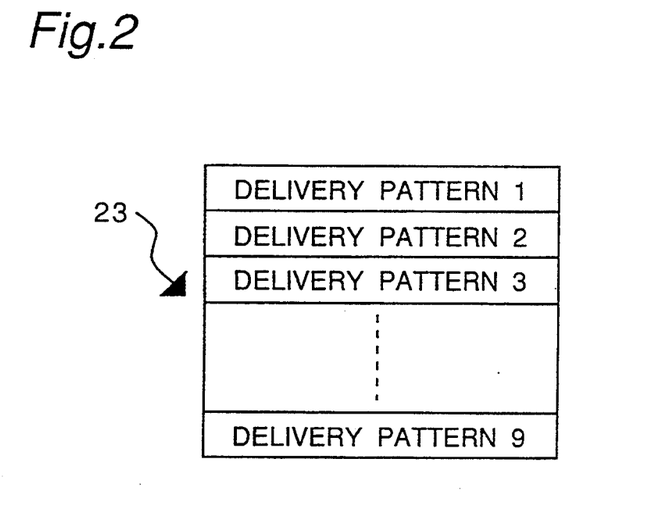
FIG. 2 is an illustration explaining contents stored in a PDP storage section of a RAM incorporated in the infusion apparatus of FIG. 1.

As shown in FIG. 2, the PDP storage section 23 can store maximum nine delivery patterns. Assuming that the delivery patterns are numbered 1, 2, ... 9, delivering of an infusion fluid starts with the delivery pattern 1. After completing the delivery of the scheduled volume in the delivery pattern 1, the apparatus automatically starts delivering the infusion fluid according to the delivery pattern 2. Subsequently, the apparatus continues to deliver the infusion fluid according to the following delivery patterns up to the delivery pattern 9. When fewer patterns are programmed, the apparatus stops its pumping operation when a non-programmed pattern is reached. The non-programmed pattern is discerned when an unpractical infusion rate of 0 ml/hr is read out from the PDP storage section 23. This method of delivering an infusion fluid using a combination of a plurality of delivery patterns programmed by the user is referred to as PDP (Program Delivery Profile) method, and an infusion mode in which programming of the delivery patterns is carried out and the infusion fluid is delivered according to the programmed plural patterns is referred to as PDP mode. On the other hand, another infusion mode in which only a single pattern is set and infusion is carried out according to this single pattern, as conventionally done, is referred to as one-pattern delivery mode herein. Selection of the PDP mode or the one-pattern delivery mode is effected by the operation of the mode selector 4a provided on the key panel 4.

The first storage section 21, which is the same as that of the conventional apparatus of FIG. 7, stores a fundamental delivery pattern (infusion rate: 125 ml/hr, volume to be infused: 250 ml) as shown in FIG. 8. TABLE 1 below shows an example of nine delivery patterns stored in the PDP storage section 23, the nine delivery patterns having been prepared on the basis of the fundamental delivery pattern stored in the first storage section 21.

TABLE 1

|  | Infusion rate Ri | Volume to be infused Vi |
|---|---|---|
| Delivery pattern 1: | 15 ml/hr | 4 ml |
| Delivery pattern 2: | 40 ml/hr | 4 ml |
| Delivery pattern 3: | 80 ml/hr | 4 ml |
| Delivery pattern 4: | 100 ml/hr | 3 ml |
| Delivery pattern 5: | 125 ml/hr | 220 ml |
| Delivery pattern 6: | 100 ml/hr | 3 ml |
| Delivery pattern 7: | 80 ml/hr | 4 ml |
| Delivery pattern 8: | 40 ml/hr | 4 ml |
| Delivery pattern 9: | 15 ml/hr | 4 ml |

Figure 3:
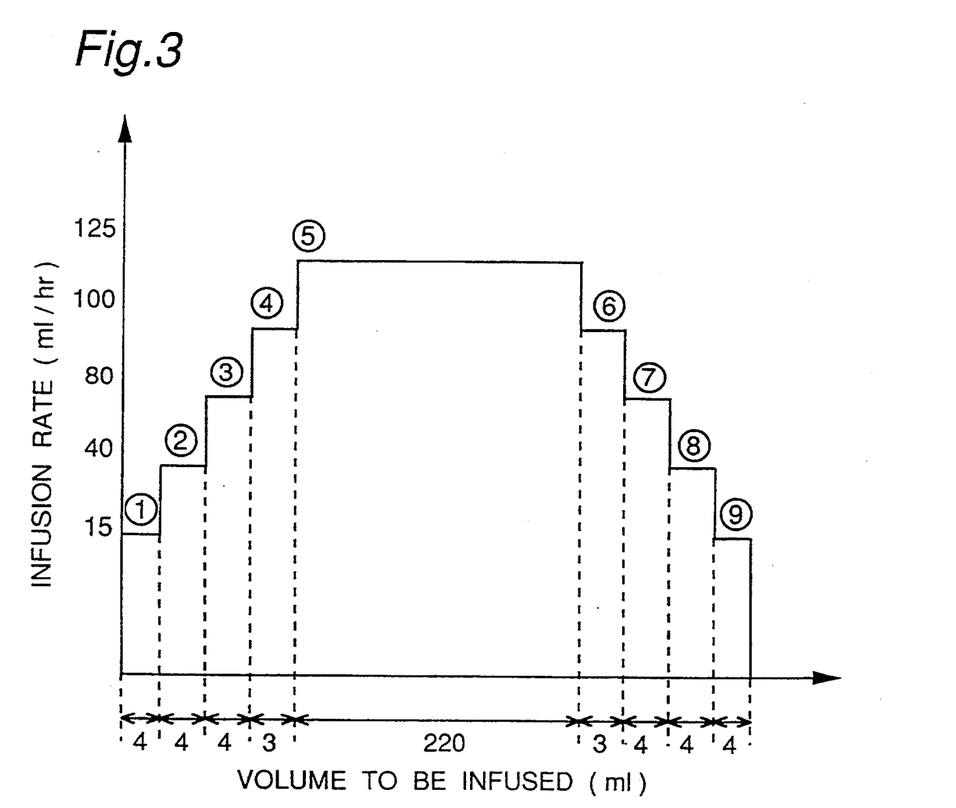
FIG. 3 is a graph showing a delivery profile obtained by the contents stored in the PDP storage section of FIG. 2.

The nine delivery patterns above are graphed in FIG. 3 wherein numbers 1–9 surrounded by a circle indicate the delivery patterns' numbers. As shown in the graph of FIG. 3, in the initial stage of the infusion, the infusion rates are increased in steps according to the delivery patterns 1 to 4 until the infusion rate of 125 ml/hr of the fundamental delivery pattern and also of the delivery pattern 5 is reached. On the other hand, in the final stage of the infusion, the infusion rates are decreased in steps according to the delivery patterns 6 to 9. As a whole, a total amount of 250 ml, which is prescribed by the fundamental delivery pattern, is delivered.

Figure 4:
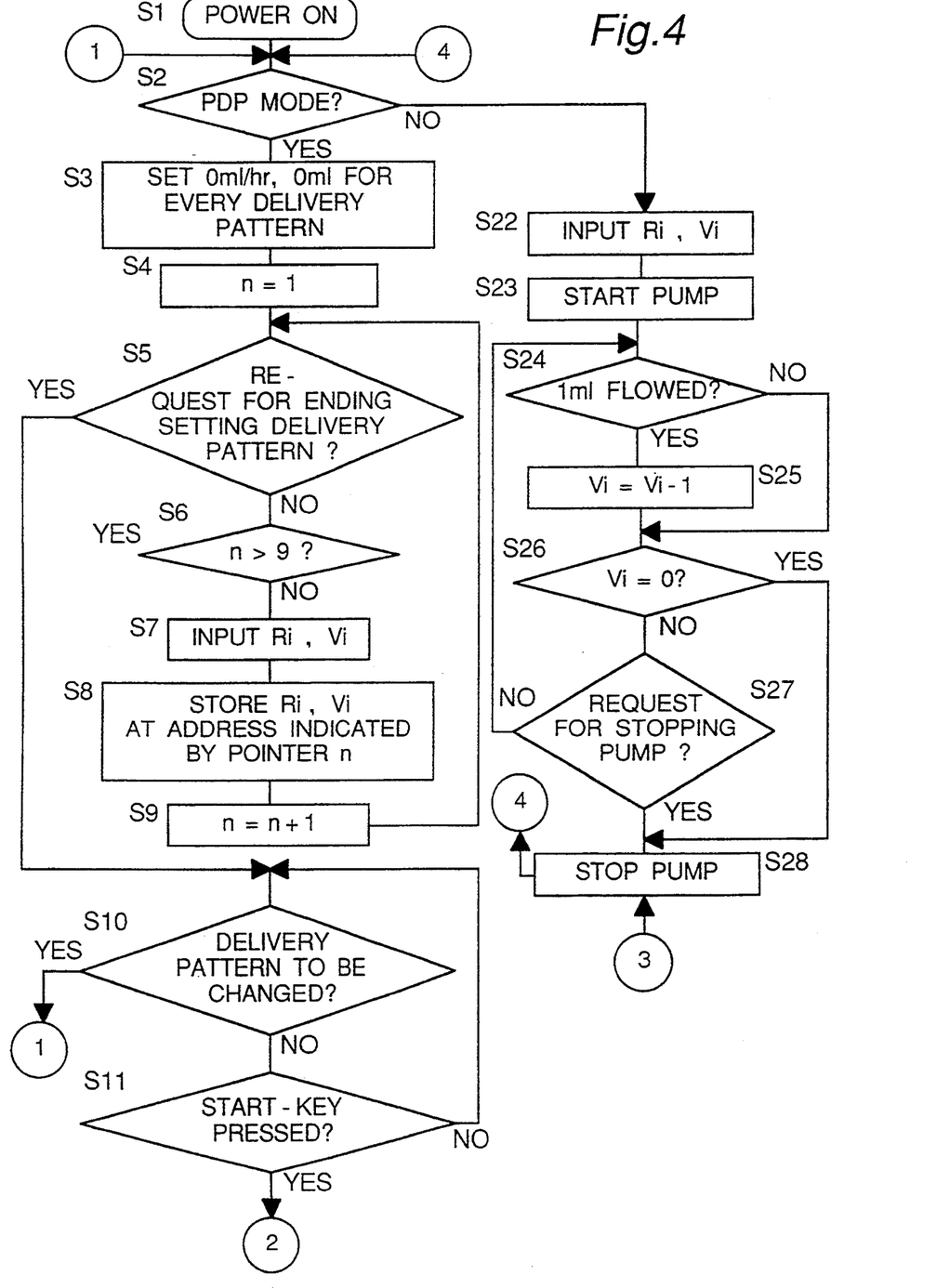
FIG. 4 is a flowchart of the operation of the infusion apparatus of FIG. 1.
Figure 5:
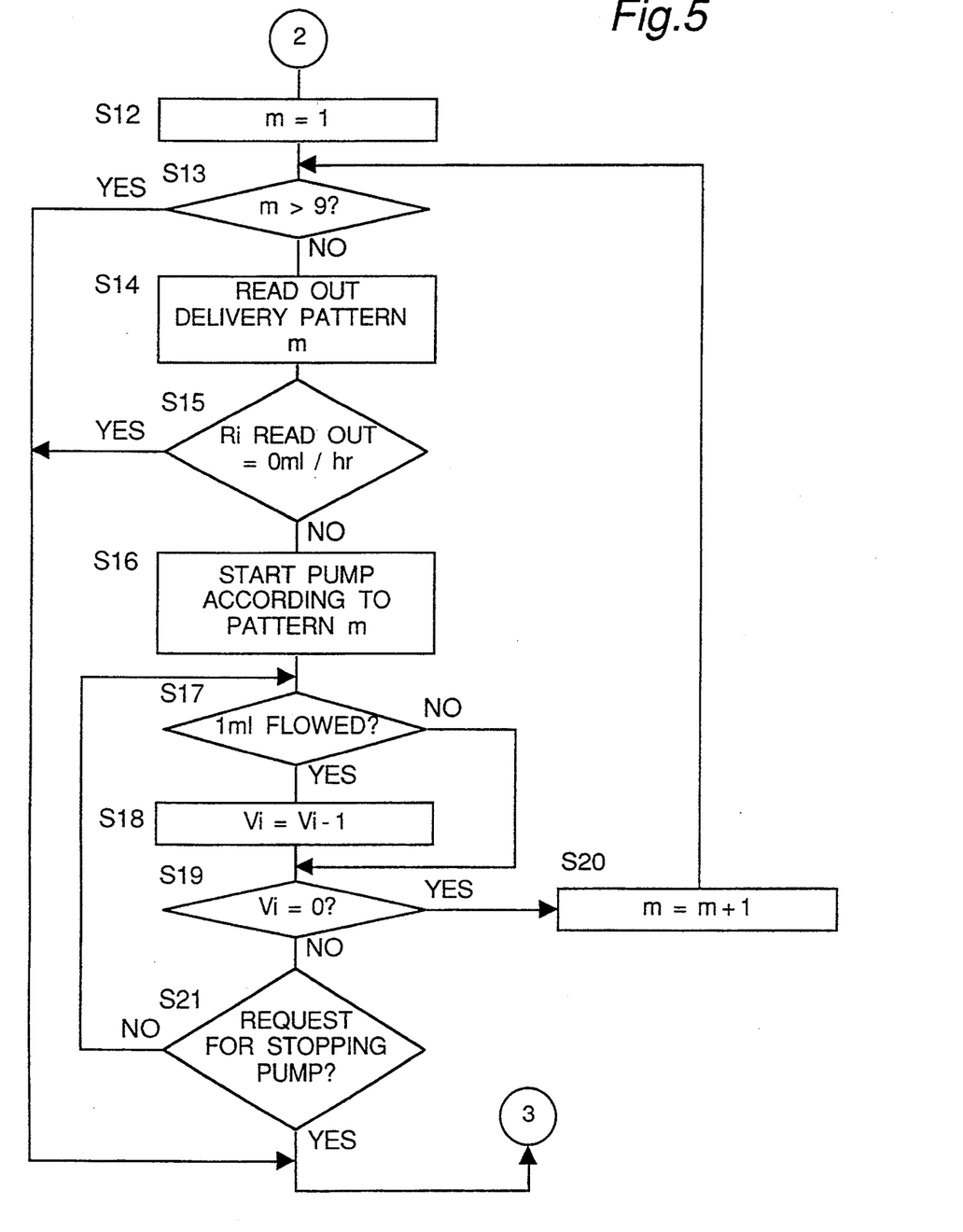
FIG. 5 is a flowchart continued from the flowchart shown in FIG. 4.

The following describes the operation of the present embodiment with reference to the flowcharts shown in FIGS. 4 and 5.

First, the power is turned on at step S1. Then the infusion apparatus 100 requests an operator to input parameter values of the infusion rate and volume to be infused. At this time, the operator is required to make a selection between the one-pattern delivery mode according to the conventional technique and the PDP mode of the invention. The two modes can be operated in sequence.

When the conventional one-pattern delivery mode is selected, an infusion rate Ri and a volume to be infused Vi are inputted at step S22, and the pump mechanism 8 is started to deliver an infusion fluid of the set volume Vi at the constant infusion rate Ri at step S23. Then it is checked at step S24 whether or not an incremental unit of fluid (1 ml in this case) has taken place. The incremental unit of fluid can be detected by detecting a predetermined amount of motor rotation of the pump mechanism 8 by the rotation detector 10. If it is determined at step S24 that 1 ml of the infusion fluid has taken place, the program proceeds to step S25 at which 1 is subtracted from the initially inputted value of the volume to be infused Vi, and a new value obtained through this subtraction is set as a renewed volume (Vi=Vi−1). Next, at step S26, it is discriminated whether or not the renewed volume to be infused Vi is zero. If yes, the pump mechanism 8 is stopped operating at step S28 and the program returns to step S2. However, when the renewed volume to be infused Vi is not zero, it is checked at step S27 whether stopping or halting of the pumping operation has been requested by the stop key on the key panel 4 or due to occurrence of some alarm.

Next, reference is made to the case in which the PDP mode is selected at step S2.

First, at step S3, all memory portions of the PDP storage section 23 are initialized to have a value of zero. That is, 0 ml/hr and 0 ml are set as infusion rate Ri and volume to be infused Vi for every delivery pattern. This initialization of the PDP storage section 23 is done for detection at step S15 of the case in which a delivery pattern is not set. After completion of the initialization of the PDP storage section 23, the program proceeds to step S4 at which an initial value of 1 is set for a pointer n ($1 \leq n \leq 9$ in the present embodiment) which indicates an address at which a delivery pattern n is written into the PDP storage section 23.

As long as a key-inputted request to end setting of values of the delivery patterns is not detected at step S5 and it is not determined at step S6 that data Ri and Vi for all of the nine delivery patterns have been set, an infusion rate Ri and a volume to be infused Vi are inputted for the respective delivery pattern at step S7. Subsequently, at step S8, the inputted values Ri and Vi are written into the PDP storage section 23 at a respective address pointed to by the pointer n. Once the values Ri and Vi are set for the nth delivery pattern at step S8, the pointer n is incremented by one at step S9. The steps S5 to S9 are repeated until a request to end setting of the delivery patterns is detected at step S5 or until it is determined at step S6 that setting for the last delivery pattern is completed. When there is a request to end setting of the delivery patterns or when settings for all delivery patterns get stored in the PDP storage section 23, the program proceeds to step S10. At step S10, before starting the pumping operation, it is confirmed whether the delivery patterns once inputted should not be changed or not. Then, the CPU 18 waits for the start key to be pressed. If it is judged at step S11 that the start-key has been pressed, then the program proceeds to step S12.

At step S12, an initial value of 1 is set for a pointer m ($1 \leq m \leq 9$) which indicates an address at which a delivery pattern m is read out from the PDP storage section 23. At step S13, it is discriminated whether m is larger than 9 or not. If m is judged to be greater than 9 at step S13, it is regarded that delivering in all of the nine delivery patterns has been completed. Therefore the program skips to step S28 at which the pump mechanism 8 stops delivering the infusion fluid.

On the other hand, so far as m is not greater than 9, the infusion rate Ri and the volume to be infused Vi of the delivery pattern m pointed to by the pointer m are read out from the PDP storage section 23 at step S14. Then at step S15, it is checked whether or not the infusion rate Ri read out is 0 ml/hr. When the infusion rate Ri is 0 ml/hr, it is found that the number of the programmed patterns is smaller than 9. Therefore, the program proceeds to step S28 and the pumping operation is stopped. When the infusion rate Ri read out at step S14 is not 0 ml/hr, the program proceeds to step S16 to start the pumping operation to deliver the infusion fluid according to the read-out delivery pattern m.

Next, at step S17, it is judged whether or not the infusion fluid of 1 ml (an incremental unit) has taken place. When 1 ml of the infusion fluid has taken place, one (1) is subtracted from the value Vi and a value obtained through this subtraction is newly set as volume to be infused Vi (Vi=Vi−1), at step S18. When the value Vi is reduced to zero at step S19, the delivery pattern readout pointer m is incremented by one at step S20 and the program returns to step S13 to read out the next delivery pattern from the PDP storage section 23. The stepping motor keeps driving the pump mechanism 8 unless it is found at step S21 that stopping of the pumping operation has been requested, more specifically, that the stop key on the key panel 4 has been pressed or that some alarm has occurred.

As obvious from the above description, the infusion apparatus of the present embodiment is designed such that the RAM 19 has the PDP storage section 23 capable of storing a plurality of delivery patterns defining combinations of infusion rates Ri and volumes to be infused Vi, that such a plurality of delivery patterns are stored in the PDP storage section 23 through key-input from the key panel 4, and that infusion is performed according to the delivery patterns automatically read out in sequence from the PDP storage section 23. Accordingly, it is possible to perform infusion in a manner suitable for the condition of the patient and the kind of medication.

The number of delivery patterns to be stored in the PDP storage section 23 is not limited to nine.

The invention being thus described, it will be obvious that the same may be varied in many ways. Such variations are not to be regarded as a departure from the spirit and scope of the invention, and all such modifications as would be clear to one skilled in the art are intended to be included within the scope of the following claims.

What is claimed is:

1. A method of delivering an infusion fluid to infuse the infusion fluid into a patient by the use of a peristaltic pump comprising the steps of:
   (a) providing a one pattern delivery mode where the infusion fluid is delivered in accordance with a single delivery pattern and a program delivery profile mode where the infusion fluid is delivered in accordance with a plurality of delivery patterns,
   (b) selecting said one pattern delivery mode for the infusion of fluid;
   (c) inputting only the single delivery pattern;
   (d) storing said single delivery pattern inputted in the step (c);
   (e) reading out said single delivery pattern stored in the step (d); and
   (f) delivering the infusion fluid according to said single delivery pattern read out in the step (e).

2. The method of claim 1, further comprising the steps of:
   (g) selecting said program delivery profile mode for the infusion of fluid;
   (h) inputting the plurality of delivery patterns;
   (i) storing said plurality of delivery patterns inputted in the step (h);
   (j) reading out said plurality of delivery patterns stored in the step (i) in sequence; and
   (k) delivering the infusion fluid according to said plurality of delivery patterns read out in sequence in steps (j).

3. The method of claim 1, further including the step of (g) operating a peristalic pump for performing the delivering in step (f).

4. The method of claim 3 wherein the step (g) includes contacting a tube for carrying the infusion fluid.

* * * * *

UNITED STATES PATENT AND TRADEMARK OFFICE
CERTIFICATE OF CORRECTION

PATENT NO. : 5,389,071
DATED : February 14, 1995
INVENTOR(S) : Masafumi Kawahara, et. al.

It is certified that error appears in the above-indentified patent and that said Letters Patent is hereby corrected as shown below:

Title page,
ITEM 73, change "Assignee: Sharp Kabushiki Kaisha, Osaka, Japan" to read --Assignee: Sharp Kabushiki Kaisha, Osaka, Japan and Baxter International, Inc., Deerfield, Illinois, USA--.

Signed and Sealed this

Twelfth Day of September, 1995

*Attest:*

BRUCE LEHMAN

*Attesting Officer*  *Commissioner of Patents and Trademarks*